United States Patent
Jörnéus et al.

(10) Patent No.: US 6,419,489 B1
(45) Date of Patent: Jul. 16, 2002

(54) ARRANGEMENT FOR USE IN A SYSTEM WITH A RANGE OF DENTAL SCREWS, AND THE RANGE OF DENTAL SCREWS

(75) Inventors: Lars Jörnéus, Frillesås; Halvar Hanssen, Göteborg, both of (SE)

(73) Assignee: Nobel Biocare AB, Gothenburg (SE)

(*) Notice: Subject to any disclaimer, the term of this patent is extended or adjusted under 35 U.S.C. 154(b) by 0 days.

(21) Appl. No.: 09/308,200
(22) PCT Filed: Aug. 25, 1997
(86) PCT No.: PCT/SE97/01397
  § 371 (c)(1),
  (2), (4) Date: May 14, 1999
(87) PCT Pub. No.: WO98/12982
  PCT Pub. Date: Apr. 2, 1998

(30) Foreign Application Priority Data

Sep. 24, 1996 (SE) ................................................ 9603477

(51) Int. Cl.⁷ .............................. A61C 3/00; A61C 8/00
(52) U.S. Cl. ........................................ 433/141; 433/173
(58) Field of Search ................................. 433/141, 173, 433/174, 172

(56) References Cited

U.S. PATENT DOCUMENTS

| | | | | |
|---|---|---|---|---|
| 4,856,994 A | * | 8/1989 | Lazzara et al. | 433/173 |
| 5,105,690 A | * | 4/1992 | Lazzara et al. | 81/436 |
| 5,515,754 A | * | 5/1996 | Elkins | 81/177.9 |
| 5,622,500 A | * | 4/1997 | Niznick | 433/173 |

\* cited by examiner

*Primary Examiner*—Nicholas D. Lucchesi
(74) *Attorney, Agent, or Firm*—Connolly Bove Lodge & Hutz LLP

(57) ABSTRACT

A system which provides a range of dental screws. The same screw tightener is used to tighten different screws, of different constructions. Each screw is provided with an internal recess which operates with the screw tightener. The recess has elements extending inward toward the center axis of the screw which cooperate with the screw tightener. Bearing capacity is provided by a wedging action between the screw tightener and recess, and a driving function occurs through actually extending elements within the recesses.

20 Claims, 2 Drawing Sheets

 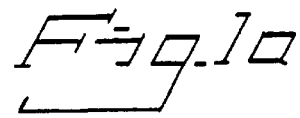
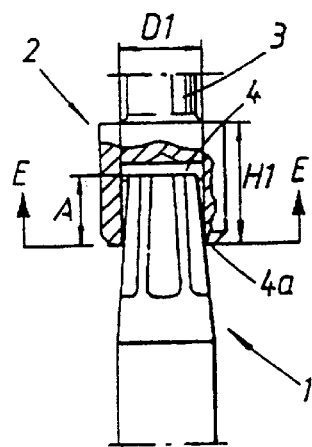 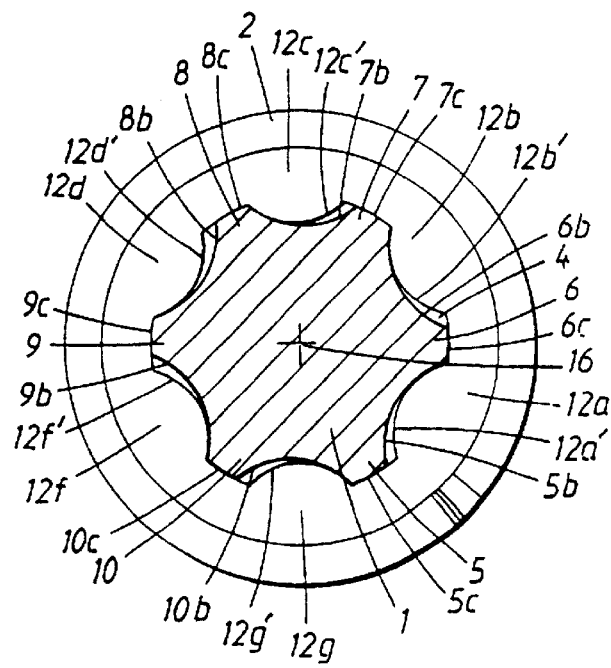
 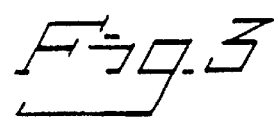 
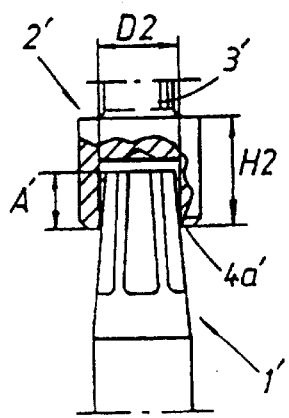 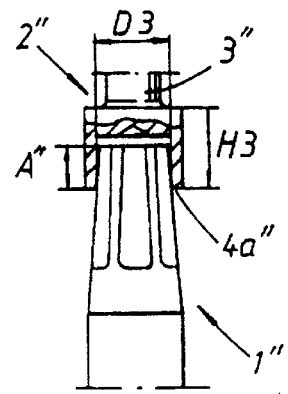 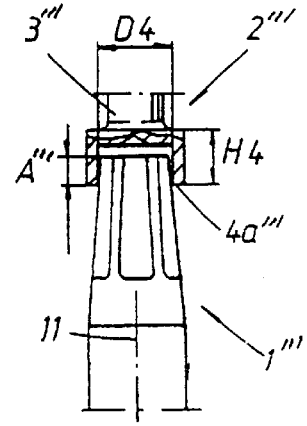

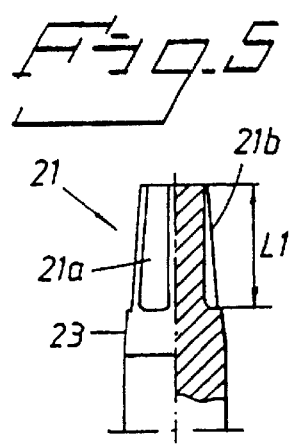
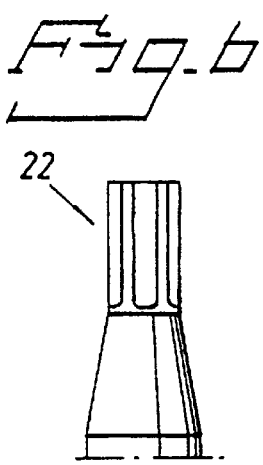
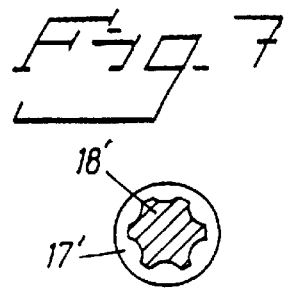
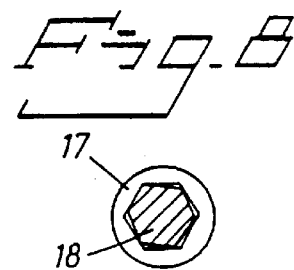
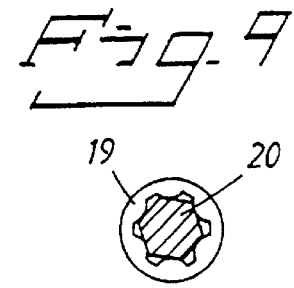
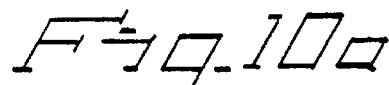
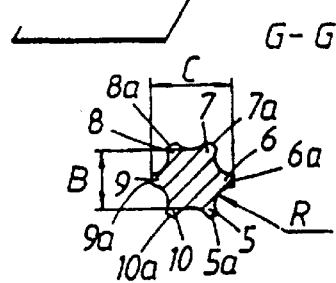
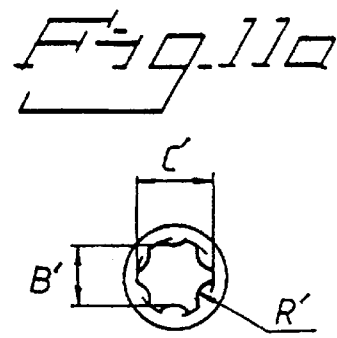
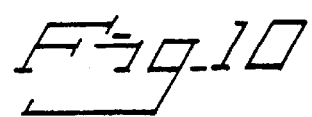
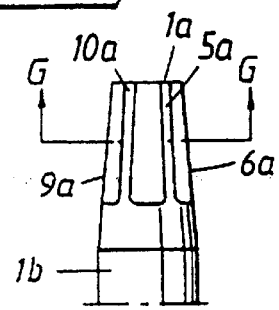

ARRANGEMENT FOR USE IN A SYSTEM WITH A RANGE OF DENTAL SCREWS, AND THE RANGE OF DENTAL SCREWS

TECHNICAL FIELD

The present invention relates to an arrangement used in a system with a range of dental screws for tightening the screws by means of one and the same screw tightener or screwdriver, which screws in this case consist of different types and have different constructions in terms of screwhead height, screw length, thread diameter, etc. Each screw in this case has an internal recess via which the cooperation with the screw tightener is afforded. Each recess has elements extending inwards towards the centre axis of each screw, and the screw tightener has, at its end which can cooperate with the screws, parts which can cooperate with the elements during screw tightening. The said elements in each recess extend, in the longitudinal direction of the recess, essentially parallel to the longitudinal axis of the screw. The invention also relates to a range of dental screws.

PRIOR ART

It is known that in the case of high turning moments, the tightener or screwdriver must be deeply engaged in the screwhead so that the contact surfaces between the screw and the tightener are large. It is also known that in the case of dental products there is a requirement to be able to transport the screw in question, held on the tip of the tightener or screwdriver, without any risk of the screw falling off. It has hitherto been proposed, inter alia, to provide each screwhead with internal elastic elements arranged at or in the recess in order to ensure the said bearing capacity function. It has also been proposed to make available a relatively large number of different tighteners or screwdrivers which are intended to match a small number of screws. This has led to a high degree of complexity in the system for application of implants.

DISCLOSURE OF THE INVENTION
TECHNICAL PROBLEM

There is general interest in reducing the number of different instruments which need to be used in the application of dental implants. There is therefore a requirement for one and the same tightener or screwdriver to be able to be used for a large number of different screws. Likewise, it must also be possible to satisfy the requirement for the smallest possible dimensions.

There is also a requirement for the screws and/or the screwdriver to be able to be produced in a conventional manner, without using elastic elements, O-rings or the like.

The object of the invention is to solve the above problems, inter alia, and it proposes new ways of creating effective driving and bearing capacity functions in this context. In the case of high driving moments, a large degree of penetration of the tightener into the respective screwhead is required, and the invention is based on the recognition that the height of the screwhead or the depth of the recess must be set in relation to the driving moment requirement, while at the same time satisfying the bearing capacity function. The invention solves this problem too by proposing an arrangement in which the number of tighteners or screwdrivers is balanced against the requirements regarding tightening moment and the desire for the smallest possible dimensions.

There is also a requirement to keep down the costs of manufacturing the screw range. The invention solves this problem too.

The feature which is principally regarded as characterizing an arrangement according to the invention is that the circular cross-section of the screw tightener, at the outsides of the said parts, widens slightly conically from the said end, at the same time as the surfaces of the parts bearing against the elements are essentially parallel to corresponding surfaces of the elements.

In one embodiment, the invention is characterized by the fact that the recesses in the screws operated by the tightener are adapted, in accordance with each tightening moment effected by the tightener, by selecting different screwhead heights and on the basis that the smallest possible dimensions are to be retained. A bearing capacity or firm wedging required between the tightener and the respective screw is also provided in this case.

An alternative way of looking at the invention shows that it can be characterized by the fact that the tightener and the screws work with two functions, where the first function is a tightening function and the second function is a bearing capacity function consisting of a firm wedging occurring between the tightener and each screw when the tightener is introduced into the recess of the screw, and that the first and second functions are in this case mechanically separate.

In further developments of the inventive concept, it is proposed that by selecting larger recesses, the tightener is able to penetrate deeper down into each recess, and vice versa. In one embodiment, the recesses of the screws are selected with increasing diameter values seen across the whole range, and the increasing values meet increasing requirements of high turning moments, and vice versa. In one embodiment, the height of the screwheads is set in relation to the driving and bearing capacity functions, so that higher screwhead heights are used for greater driving force, and vice versa, the bearing capacity being effected by the cooperation between the screwdriver and the screw material at the mouth of each recess, so that the required bearing capacity is present independently of the height of the screwhead.

A range of dental screws is characterized, inter alia, by the fact that each screw is arranged to cooperate with a screw tightener whose circular cross-section, at the outsides of the parts, widens slightly conically from the end. Also present on the elements there are cooperating surfaces which are essentially parallel to corresponding cooperating surfaces on the parts of the screw tightener. The range can also be characterized, inter alia, by the fact that each screw is arranged for two functions, namely a tightening function and a bearing capacity function, which functions are mechanically separate.

Further characteristics and developments are evident from the subclaims which follow. Thus, for example, the screw diameters are selected in the range from 1 to 3 millimeters, preferably from 1.4 to 2.5 millimeters.

ADVANTAGES

A great benfit is gained by virtue of the fact that the number of tighteners or screwdrivers can be reduced for the same number of different screws. The manufacturing accuracy or the tolerances are adapted to the driving and bearing capacity requirements, which affords advantages from the manufacturing and cost aspects seen across the whole range. The invention is based on the use of tighteners of the screwdriver type, but the screws in question can also be operated using conventional hexagonal drivers (multi-edge drivers).

DESCRIPTION OF THE FIGURES

A presently proposed embodiment of an arrangement which has the significant characteristic features of the invention will be described hereinbelow with reference to the attached drawings, in which:

FIGS. 1–4 show, in vertical views, those parts of a tightener or screwdriver which can cooperate with screws of different types, the tightener or screwdriver end engaging in an internal recess in each screw, and the screwdriver in question being able to operate different types of screws, FIGS. 5–6a show, in vertical and end views, front parts of screwdrivers of the novel design and of the known design, respectively, so as to illustrate the mechanical separation of the driving and bearing capacity functions in the first-mentioned case, FIGS. 7–9 show, in different end views, screwheads operated by conventional hexagonal spanners, FIGS. 10–10a show, in vertical and end views, and separate from the screw, the front parts of a screwdriver of the first embodiment, and FIGS. 11–11a show, in vertical and end views, and separate from the screwdriver, a screw according to FIG. 4.

DETAILED EMBODIMENT

FIG. 1 shows the front parts of a tightener labelled 1. The tightener is partially engaged in a screwhead 2, the screw part of which is partly shown by 3. The screwhead has an internal recess 4. The screwhead has a height H1 and the internal recess has a diameter D1. FIGS. 2, 3 and 4 show in a corresponding manner that the same tightener 1', 1" and 1''', respectively, is brought into engagement with other types of screws 2', 2" and 2''', respectively, which in a corresponding manner have screw parts 3', 3" and 3''', respectively. In this case, the recesses have the diameters D2, D3 and D4, respectively, and the heights H2, H3 and H4, respectively.

FIG. 4 shows the screwdriver 1''' in its entirety, its front parts being brought into engagement with a further type of screw 2''' which has a screw part 3''', recess diameter D4 and height H4. The different FIGS. 1–4 show that there can be different degrees of engagement A, A', A" and A''', respectively.

FIGS. 1a and 10, 10a show the design of the tightener at the end which can cooperate with the respective screwhead. The tightener or the screwdriver is provided with six radially protruding parts 5, 6, 7, 8, 9 and 10. The outsides 5a, 6a, 7a, 8a, 9a and 10a of these parts are cone-shaped and widen from the end surface 1a of the tightener (see FIG. 4) out towards the holding part 1b of the tightener (see FIG. 4). This conicity of the parts 5–10 forms part of a bearing capacity function which is described 15 hereinafter. The said parts 5–10 are connected to one another via arc-shaped portions 5b, 6b, 7b, 8b, 9b and 10b. These portions extend essentially parallel to the centre axis 11 of the tightener (cf. also FIG. 4). The arc-shaped portions 5b–10b form part of the driving function between the tightener and the respective screw according to FIGS. 1–4, 11 and 11a.

FIG. 10a indicates a radius R for each arc-shaped portion 5b–10b (cf. FIG. 1a). In the present illustrative embodiment, this radius is selected as 4.0 +0.05 mm. FIG. 10a also indicates a distance B between diametrically opposite arc-shaped portions (7b and 10b according to FIG. 1a). In the present case, B is selected as 1.18+0.02. FIG. 10a also shows a diameter C between the outsides of two diametrically opposite parts (in this case 6a and 9a). In the illustrative embodiment, C is selected as 1.48±0.02. According to FIGS. 11–11a, this is produced with corresponding tolerances at corresponding values for B', C'and R', respectively.

FIG. 1a shows the screw 3 in cooperation with the tightener or screwdriver 1 applied in the internal recess 4 of the screw 2, as above. Compare also FIGS. 11 and 11a. The screw is designed with elements 12a, 12b, 12c, 12d, 12f and 12g which extend inwards towards the centre 16 and which are formed with arc shapes matching the arc shapes of the parts 5b–10b. These elements 12a–12g extend parallel to the longitudinal axis 16 of the nut/tightener. These elements form part of the driving function between tightener and nut. The surfaces of the elements 12a–12g are shown by 12a', 12b', 12c', 12d', 12f'and 12g'. These elements or surfaces cooperate with the surfaces 5b–10b according to FIG. 1a. This figure shows a case where the tolerance between the elements 12a–12g of the screw and the portions 5a–10a of the tightener is small. In this case, the radii R for the elements on the screws and the parts on the tightener are formed with great precision. The bearing capacity which is essentially or completely independent of the driving surfaces is effected by the screwdriver's surfaces 5c, 6c, 7c, 8c, 9c, 10c at the mouth 4a of the recesses 4 (see FIG. 1). The bearing capacity is effected by means of the firm-wedging function between the material of the screwdriver and the respective screw concerned.

FIG. 6 shows the case where the tolerances between the said elements and parts are greater. Thus, the radius R for the parts according to FIG. 4a is 0.375, while the radius for the elements according to FIG. 5 is =0.425.

The tolerance between the elements and the parts in accordance with the above can be varied. In an alternative case, the radius R=0.85 mm, while radius R for the elements is=0.45 mm. FIGS. 1–4 illustrate the different depths of penetration of the screwdrivers into different screws. The bearing capacities are illustrated for the above case by 4a', 4a" and 4a'''.

FIG. 7 shows the case where a screw 17' is acted upon by a conventional cross-slotted screwdriver 18'.e.

FIG. 8 shows the prior art in which a screw 17 is operated by a conventional hexagonal spanner 18. In accordance with FIG. 9, the screw design 19 according to the invention can be operated by such a hexagonal spanner 20. The depth of penetration for such hexagonal spanners can be made different in this case too.

According to FIGS. 1–4, the heights H1–H4 are set in relation to the depths of penetration A'–A'''. A greater value of Hi gives a greater depth of penetration. Exceptions may however be possible.

Screwdrivers which can operate the screws in accordance with the above are indicated by 21 and 22 in FIGS. 5a and 6a, respectively. The length of the driving and bearing capacity surfaces 21a and 21b is indicated by L1 in the case according to FIGS. 5 and 5a. In the case according to FIG. 5 there is a short, cone-shaped part 23 which connects the surfaces 21a and 21b. FIGS. 5, 5a show how the driving and bearing capacity surfaces are mechanically separated. The screwdriver 22 belongs to the prior art and is intended to act on screwheads according to FIG. 7. The bearing capacity function by means of inclined/cone-shaped surfaces is not present here, which means that there are substantial manufacturing demands in order to achieve the bearing capacity. In this case, the driving and bearing capacity functions are not separated.

The invention is not limited to the embodiment which has been shown hereinabove by way of example, but instead can be modified within the scope of the attached patent claims and the inventive concept.

What is claimed is:

1. Arrangement used in a system with a range of dental screws for tightening screws of different types comprising a screw tightener and screws having an internal recess which cooperates with the screw tightener, each of said recesses having elements extending inwards towards the center axis of each screw, the screw tightener having at an end which cooperates with the screws, parts which cooperate with the elements during screw tightening, the elements in each recess extend, in the longitudinal direction of the recess, substantially parallel to the longitudinal axis of the screw, the screw tightener having a circular cross-section, at the outsides of the parts, widens slightly conically from said end, at the same time as the surfaces of the parts bearing against the elements are essentially parallel to corresponding surfaces of the elements.

2. Arrangement according to claim 1 wherein screws are provided having larger recesses so the tightener is able to penetrate deeper into each recess.

3. Arrangement according to claim 2, wherein the recesses of the screws are selected with increasing diameter values seen across the whole range, and wherein the increasing values meet increasing requirements of high turning moments, and vice versa.

4. Arrangement according to claim 2, wherein in cases where a high tightening moment is required, the screwhead height and/or the recess depth is/are selected so as to establish sizes of formed driving surfaces, i.e. high tightening moments are assigned correspondingly large driving surfaces.

5. Arrangement according to claim 1 wherein the recesses of the screws are selected with increasing diameter values (D1, d2, D3, D4) for increasing the requirements of high turning moments.

6. Arrangement according to claim 5, wherein the higher turning moments within the screw range are of the order of magnitude of 50 Newton centimeter.

7. Arrangement according to claim 6, wherein in cases where a high tightening moment is required, the screwhead height and/or the recess depth is/are selected so as to establish sizes of formed driving surfaces, i.e. high tightening moments are assigned correspondingly large driving surfaces.

8. Arrangement according to claim 5, wherein in cases where a high tightening moment is required, the screwhead height and/or the recess depth is/are selected so as to establish sizes of formed driving surfaces, i.e. high tightening moments are assigned correspondingly large driving surfaces.

9. Arrangement according to claim 1, wherein in cases where a high tightening moment is required, the screwhead height and/or the recess depth is selected so as to establish sizes of formed driving surfaces wherein high tightening moments are assigned correspondingly large driving surfaces.

10. Arrangement according to claim 1, wherein the screw diameters are of the order of magnitude of 1–3 millimeters.

11. Arrangement according to claim 1 wherein the heights (H1, H2, H3, H4) of the screwheads are set in relation to the driving functions, so that higher screwhead heights (H1, H3) are used for greater driving force.

12. Arrangement used in a system with a range of dental screws for tightening screws of different types and different constructions comprising: a screw tightener and screws having an internal recess which cooperate with the screw tightener, each recess having elements extending inwards towards the center axis of each screw, the screw tightener having at its end which can cooperate with the screws, parts which cooperate with the elements during screw tightening, said elements in each recess extend, in the longitudinal direction of the recess, substantially parallel to the longitudinal axis of the screw, wherein the tightener and the screws work with two mechanically separate functions, the first function is a tightening function and the second function is a bearing capacity function wedging the tightener and each screw when the tightener is introduced into the recess of the screw.

13. Arrangement according to claim 12, wherein driving functions of the tightener and of the screws are arranged with axial extents, and the bearing capacity function for the tightener utilizes cone-shaped or sloping extends.

14. Arrangement according to claim 13, wherein the bearing capacity function can be established at the mouth of the recess of each screwhead by cooperation between the screwdriver and the screw material in the firm-wedging function, the cone-shaped and sloping surfaces being arranged to effect a bearing capacity function essentially independent of the screwhead height or recess depth.

15. Arrangement according to claim 12, wherein by selecting larger recesses, the tightener is able to penetrate deeper down into each recess, and vice versa.

16. Arrangement according to claim 12, wherein the recesses of the screws are selected with increasing diameter values seen across the whole range, and wherein the increasing values meet increasing requirements of high turning moments, and vice versa.

17. Arrangement according to claim 12, wherein in cases where a high tightening moment is required, the screwhead height and/or the recess depth is/are selected so as to establish sizes of formed driving surfaces, i.e. high tightening moments are assigned correspondingly large driving surfaces.

18. Arrangement according to claim 12, wherein the screw diameters are of the order of magnitude of 1–3 millimeters, preferably 1.4–2.5 millimeters.

19. A range of dental screws which can be tightened by means of one of the same screw tightener comprising a screw tightener and different types of screws which have different screwhead height, screw length, and thread diameter, each screw having an internal recess which cooperates with the screw tightener and each recess has elements extending inwards towards the center axis of each screw to cooperate with end parts on the screw tightener, and the said elements in each recess extend, in the longitudinal direction of the recess, essentially parallel to the longitudinal axis of the screw, wherein each screw is arranged to cooperate with a screw tightener whose circular cross-section, at the outsides of the said parts, widens slightly conically form the said end, and in that surfaces locates on the elements are essentially parallel to corresponding cooperating surfaces on the said end parts.

20. A range of dental screws which can be tightened by means of one and the same screw tightener comprising a screw tightener and screws having different types and have different constructions in terms of screwhead height, screw length, thread diameter, each screw having an internal recess which cooperates with the screw tightener, and each recess has elements extending inwards towards the center axis of each screw to cooperate with end parts on the screw tightener, and said elements in each recess extend, in the longitudinal axis of the screw, each screw being arranged to work with a first tightening function and a bearing capacity function wedging of the screw in the tightener when the screw receives the tightener in its recess.

* * * * *